United States Patent [19]

Swanson

[11] 4,280,231

[45] Jul. 28, 1981

[54] ELBOW PROSTHESIS

[76] Inventor: Alfred B. Swanson, 2945 Bonnell, S.E., Grand Rapids, Mich. 49506

[21] Appl. No.: 48,682

[22] Filed: Jun. 14, 1979

[51] Int. Cl.[3] .................................... A61F 1/03

[52] U.S. Cl. .................................... 3/1.91; 128/92 C

[58] Field of Search .................................... 3/1.91, 1.911; 128/92 C

[56] References Cited

U.S. PATENT DOCUMENTS

| | | | |
|---|---|---|---|
| 3,506,982 | 4/1970 | Steffee | 3/1.91 |
| 3,728,742 | 4/1973 | Averill et al. | 3/1.911 |
| 3,852,831 | 12/1974 | Dee | 3/1.91 |
| 3,946,445 | 3/1976 | Bentley et al. | 3/1.91 |
| 3,990,118 | 11/1976 | Strickland et al. | 3/1.91 |
| 4,000,525 | 1/1977 | Klawitter | 3/1.911 |
| 4,055,862 | 11/1977 | Farling | 3/1.91 |
| 4,057,858 | 11/1977 | Helfet | 3/1.91 |
| 4,079,469 | 3/1978 | Wadsworth | 3/1.91 |
| 4,129,902 | 12/1978 | Harmon | 3/1.91 |
| 4,131,956 | 1/1979 | Treace | 3/1.91 |

FOREIGN PATENT DOCUMENTS

| | | | |
|---|---|---|---|
| 1902700 | 8/1970 | Fed. Rep. of Germany | 3/1.91 |
| 2814752 | 10/1978 | Fed. Rep. of Germany | 3/1.91 |
| 1537479 | 12/1978 | United Kingdom | 3/1.91 |

OTHER PUBLICATIONS

Swanson, *Flexible Implant Resection Arthroplasty in the Hand and Extremities,* (Book) 1973, pp. 265–286.

*Vitallium Appliances* advertisement of a Mechanical Elbow in *Journ. of Bone and Joint Surgery,* Oct. 1956.

Barr, et al., "Elbow Reconstruction with a New Prosthesis", *Journal of Bone and Joint Surgery,* vol. 47–A, No. 7, pp. 1408–1413, Oct. 1965.

*Primary Examiner*—Clifford D. Crowder

*Attorney, Agent, or Firm*—Price, Heneveld, Huizenga & Cooper

[57] ABSTRACT

A prosthesis for replacing the elbow joint includes a humeral component having a body portion defining a plurality of generally semi-circular distal bearing surfaces extending therefrom and a proximally extending intramedullary canal stem. An ulnar component has a body portion defining a convex posterior surface adapted to be received within a prepared semi-lunar notch of the ulna, a plurality of semi-circular grooves configured to matingly receive the distal bearing surfaces of the humeral component, and a distally extending intramedullary canal stem. The ulnar component further defines a laterally positioned capitulum process having a distal surface adapted to be abutted against by the head of the radius bone upon implantation. The humeral component defines an aperture and the ulnar component includes a hook-like member adapted to detachably and hingingly interconnect the components in a slipfit fashion.

15 Claims, 10 Drawing Figures

ELBOW PROSTHESIS

BACKGROUND OF THE INVENTION

The present invention relates to bone joint prostheses and more particularly to a prosthesis for the total replacement of a hinge type bone joint and which results in stable flexion and extension movements.

The bones of the human skeleton are joined by a variety of different bone joints. Joints may be classified into two main structural types, namely diarthroses and synarthroses. Diarthroses are joints having a joint cavity between the articulating surfaces of the bones. Synarthroses are joints which have tissues growing between their articulating surfaces. The tissue does not permit free movement between the articulating surfaces.

Diarthrotic joints besides having a joint cavity include a thin layer of hyaline cartilage covering the joint surfaces of the articulating bones. A sleeve-like, fibrous capsule lined with a smooth, slippery synovial membrane encases the joint. Ligaments grow between the bones to constrain and latch the bones firmly together. Diarthrotic joints permit one or more of a variety of movements including flexion, extension, abduction, adduction, rotation, circumduction and special movements such as supination, pronation, inversion, eversion, protraction and retraction.

The broad joint classification may be broken down into subtypes based upon the structural relationship of the bones at the joints and the movements involved. These subtypes include the ball and socket joint, the hinge or ginglymous joint, the pivot or trochoid joint, the condyloid joint, the saddle joint and the gliding or arthrodial joint.

Procedures have been developed for repairing severely diseased or damaged joints when significant stiffness, pain or loss of motion is present. These procedures have included arthroplasty, that is, removal of the defective bone portions and partial implant replacement, which essentially involves resurfacing of one of the articulating bone surfaces with a prosthesis. Fairly recently, total joint prostheses have been developed which entirely replace the joint. Such prosthetic devices have been employed for replacement of finger joints, knee joints and elbow joints, for example.

The elbow is a diarthrotic joint formed by articulation of the distal humerus with both the radius and the ulna. Stability depends on the shape of the joint articular surfaces and the maintenance of their coaptation by the ligaments and muscles surrounding the joint. A hinge joint exits at the ulnar humeral articulation allowing movement of flexion and extension only. The articulation between the radius and the humerus is a trochoid or pivot joint which allows nearly all movements of pronation and supination of the forearm. The distal humerus includes the trochlea which articulates with the semilunar notch of the ulna and the capitulum which articulates with the proximal surface of the radial head. The vertical margin of the radial head rotates with the radial notch of the ulna.

Repair of diseased or damaged elbow joints has included resection arthroplasty, implant replacement of the radial head, flexible implant resection arthroplasty of the elbow joint and the use of rigid metal hinge devices for arthroplasty of the elbow joint. Reconstitution with prior hinge type total prostheses has presented various problems relating to stability of the joint, loosening of the implant, excessive bone stock removal and transmission of excessive stress to the bones by the implant.

A discussion of the problems heretofore experienced and examples of some prior approaches may be found in Alfred B. Swanson, *Flexible Implant Resection Arthroplasty In the Hand and Extremities* pp. 265–286 (1973).

Prior total elbow procedures have also typically included resection of the radial head. Proximal migration of the radial shaft may occur. Such migration typically results in limitations of wrist motion, radial deviation of the hand, and prominence of the distal end of the ulna. These result in pain, instability, weakness, tiredness and a limitation on range of motion. With rheumatoid arthritis patients, postoperative complications at the wrist after radial head resection have been or may be overlooked. Such pathology is imputed to the generalized disease.

Further examples of prior elbow joint prostheses may be found in U.S. Pat. No. 3,852,831, entitled ENDOPROSTHETIC ELBOW JOINT and issued on Dec. 10, 1974 to Dee; U.S. Pat. No. 3,990,118, entitled JOINT PROSTHESIS and issued on Nov. 9, 1976 to Stickland et al; U.S. Pat. No. 4,057,858, entitled ELBOW PROSTHESIS and issued on Nov. 15, 1977 to Helfet; U.S. Pat. No. 4,079,469, entitled ELBOW JOINT ENDOPROSTHESIS and issued on Mar. 21, 1978 to Wadsworth; and U.S. Pat. No. 4,131,956, entitled ELBOW PROSTHESIS and issued on Jan. 2, 1979 to Treace.

The prosthesis disclosed in U.S. Pat. No. 4,079,469 includes a humeral component hinged by a T-slot structure to an ulnar component. The humeral component defines a lateral, hemispherical surface which replaces the capitulum. The head of the radius, which may have a head implant thereon, articulates with the hemispherical surface.

Despite the wide variety of proposals and procedures available for replacement of joints such as the elbow joint, problems have still been experienced and a need exists for an improved hinge joint possessing increased stability, which reduces the stress and strain imposed upon the adjacent bones and which simplifies the surgical procedure.

SUMMARY OF THE INVENTION

In accordance with the present invention, an articulating hinge-type prosthesis is provided whereby the problems heretofore experienced are substantially alleviated. Essentially, the prosthesis is of a semi-constraint type and includes a first component having a body defining a through aperture and a plurality of transversely spaced distally extending portions defining curved bearing surfaces. A second component includes a body defining a plurality of inwardly directed grooves dimensioned to receive the curved bearing surfaces in a tongue and groove fashion. Provision is made for detachably interconnecting the first and second components in a slipfit fashion to permit hinge-type pivotal movement of the components relative to each other through the normal range of flexion and extension.

In narrower aspects of the invention, the prosthesis is adapted for total replacement of the elbow joint and the second component includes a lateral process having a distal surface against which the radius bone may abut and articulate. The lateral process prevents proximal migration of the radius and resulting severe pain in the wrist. Also, the process eliminates direct articulation of the head of the radius with respect to the humeral component of the implant. Due to the manner of interconnection of the components, the surgical procedure is simplified. Further, since a rigid hinge pin, direct mechanical interconnection is not employed, stresses on the bone structure and on the implant components are reduced. Lateral stability of the reconstructed joint is maintained due to the configuration of the components and reconstruction of the joint ligaments after implantation.

DETAILED DESCRIPTION OF THE PREFERRED EMBODIMENT

Figure 1:
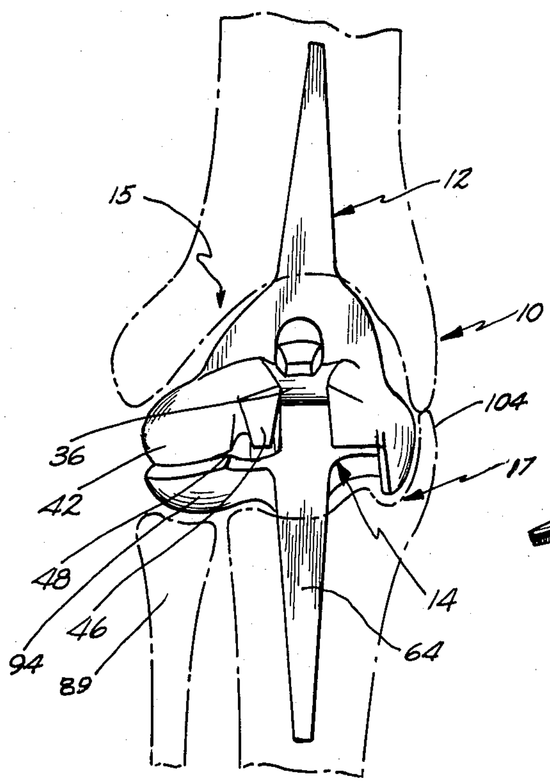
FIG. 1 is an anterior, elevational view of a prosthesis in accordance with the present invention with the humerus, ulna and radius schematically shown.
Figure 2:
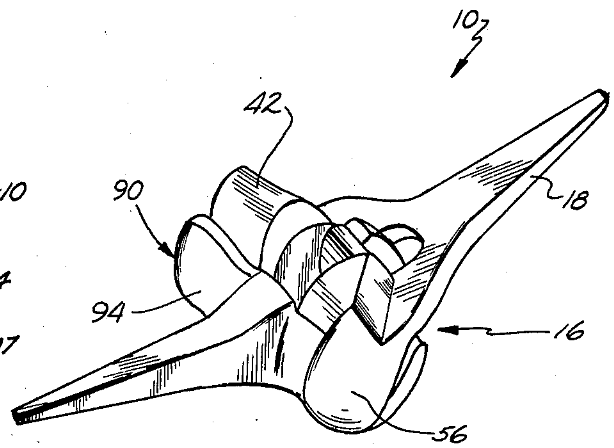
FIG. 2 is a medial, perspective view thereof.
Figure 3:
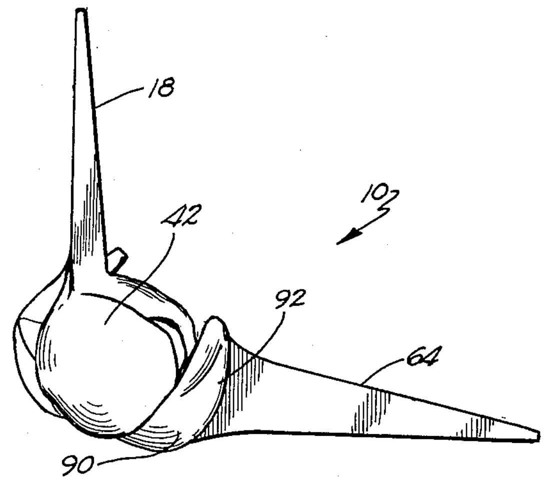
FIG. 3 is a lateral, elevational view thereof.
Figure 4:
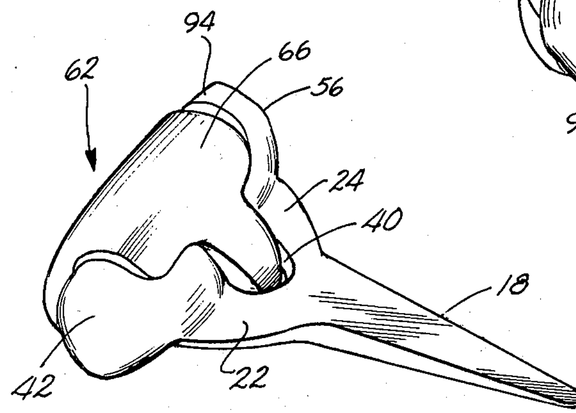
FIG. 4 is a posterior view thereof.

The preferred embodiment of a prosthesis for replacement of a hinge joint and particularly the elbow joint is illustrated in FIG. 1 and generally designated 10. Prosthesis 10 includes a first component 12 interconnected with a second component 14. Component 12 is adapted for implantation at the prepared distal end 15 of the humerus. Component 14 is adapted for implantation at the proximal end 17 of the ulna. The components are interconnected in a slipfit fashion providing stable, full range flexion and extension.

Figure 5:
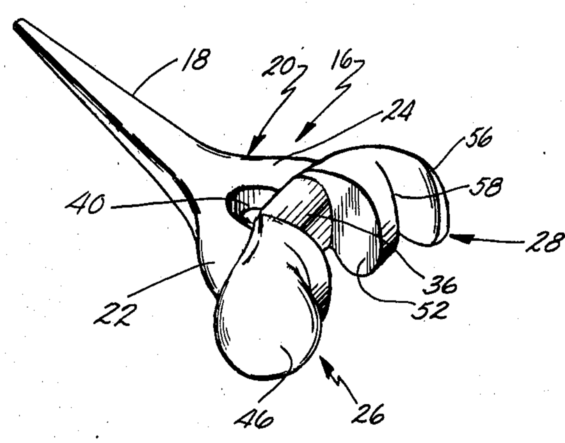
FIG. 5 is a distal, perspective view of the humeral component.
Figure 6:
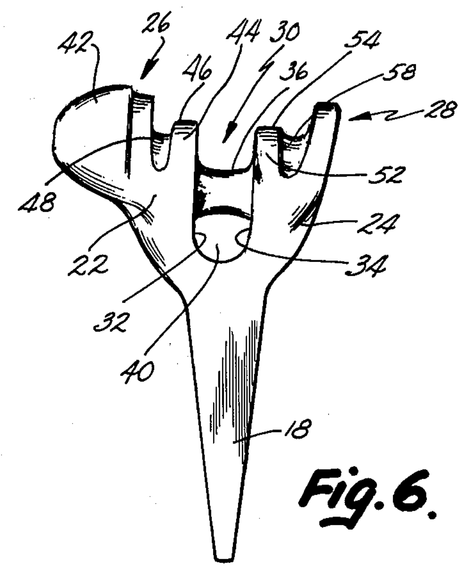
FIG. 6 is a posterior view of the humeral component.
Figure 7:
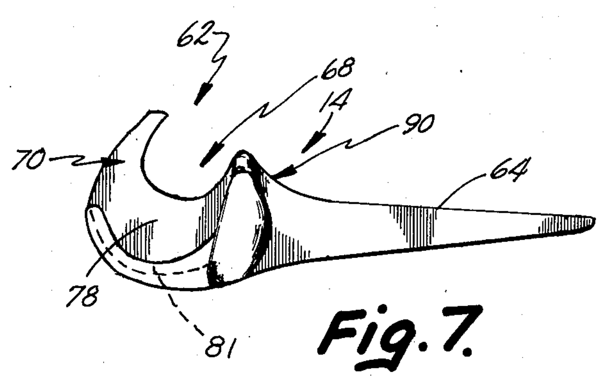
FIG. 7 is a lateral, elevational view of the ulnar component.

Humeral component 12 includes a main body or head 16 and an integral, proximally extending intramedullary canal stem 18 (FIGS. 5 and 6). Stem 18 is adapted to affix the humeral component 12 to the humerus by insertion thereof into the prepared medullary canal. Stem 18 is joined to the main body 16 at a generally planar portion 20. Planar portion 20 is bifurcated and includes arms 22, 24. Arm 22 is integral with a lateral portion 26. Arm 24 is integral with a medial portion 28. Portion 20 and portions 26, 28 define an elongated slot 30 having opposed planar, parallel sides 32, 34. The opposed sides are joined by an anteriorly positioned transversely extending, generally cylindrical cross member 36. The cross member in conjunction with the elongated slot therefore defines a proximally positioned generally rectangular aperture 40.

Lateral portion 26 includes a semi-globular, bulbous, or hemispherical and smoothly curved lateral process or member 42 and a distally extending, semi-circular flange 44. Flange 44 defines a curved bearing surface 46. Flange 44 is separated from bulbous portion 42 by a groove 48 (FIG. 6).

Medial portion 28 similarly defines a distally and radially extending flange 52 having a peripheral, semi-circular bearing surface 54. Portion 28 further defines a medially positioned, semi-circular end flange 56. Flange 56 has a radius greater than the radius of the flange portion 52 and is separated therefrom by a groove 58. As best seen in FIGS. 5 and 6, stem 18 and arms 20, 22 lie in a plane spaced posteriorly from a plane passing parallel therewith and through the centerline of cross piece 36.

Ulnar component 14 includes a main body or head portion 62 and a distally extending, integral intramedullary canal stem 64 (FIGS. 7, 8, 9 and 10). Stem 64 is generally tapered from the body rearwardly or distally and is configured to be inserted within a prepared intramedullary canal of the ulna. Body portion 62 defines a generally convex posterior surface 66 and a generally concave anterior surface 68. Extending centrally of surface 68 and anteriorly therefrom is a hook-shaped member generally designated 70. Hook-shaped member 70 includes a stem 72 and a curved portion 74 which extends from stem 72 proximally, anteriorly and then distally. Hook member 70 includes a lateral side 78 and a medial side 80.

Figure 8:
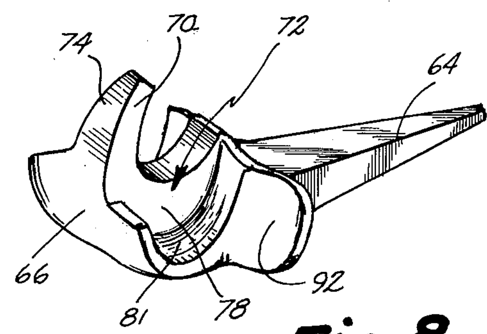
FIG. 8 is a proximal, perspective view of the ulnar component.
Figure 9:
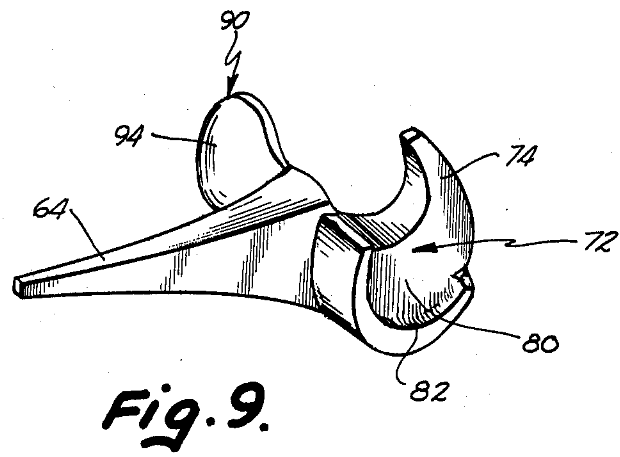
FIG. 9 is a medial, perspective view of the ulnar component.
Figure 10:
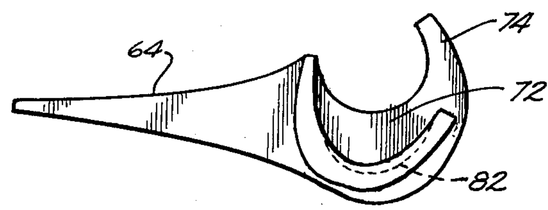
FIG. 10 is a medial elevational view of the ulnar component.

Opening through the anterior surface of the head or main body portion 62 and laterally of the hook member is a walled groove 81 (FIG. 8). Groove 81 is semicircular in cross section and is dimensioned and configured to matingly receive flange 46 of the humeral component, in a tongue and groove fashion. Opening anteriorly from a portion of main body 62 and disposed medially of the hook member is another groove 82. Groove 82 is similarly dimensioned and configured to matingly receive flange 52 in a tongue and groove fashion and hence bearing surface 54 of the humeral component. The flanges and mating grooves in the respective components permit stable, rotating relative motion between the components. The interfit between these portions of the components assures that the implant when assembled will rotate in a single plane and have adequate lateral to medial or side to side stability. The sidewalls of the flanges engage the sidewalls of the groove to insure such stability.

As seen in FIGS. 1, 2, 3 and 4, the humeral component is interconnected with the ulna component due to interaction of the hook member and the elongated slot formed in the humeral component. When the two components are positioned relative to each other in extreme flexion, the curved portion of the hook may be slipped around cross member 36 and through rectangular slot or aperture 40. The two components will then rotate through a normal range of flexion and extension without dislocation. The components are configured so that limited proximal and distal motion of the components may occur without the bearing defining flanges being removed from the grooves defined by the ulnar component. As a result, the components are not rigidly interconnected as in a permanent, direct mechanical hinge-type prosthesis employing the hinge pin. Stability is provided, in part, by reconstruction of the ligaments about the implant after implantation. The hook and aperture interconnection permits each individual component to be separately implanted and positioned in respective bones prior to interconnection. This simplifies the surgical procedure normally employed to implant a total elbow prosthesis.

When an implant is employed in the total replacement of the elbow joint and the head 89 of the radius bone (FIG. 1) is surgically removed, problems can be experienced due to proximal migration of the radius during normal use of the arm. The implant in accordance with the present invention overcomes these problems by providing a lateral process or capitulum portion 90 integral with the head of the ulnar component. Capitulum portion 90 extends generally perpendicular to the longitudinal axis of intramedullary stem 64 of the ulnar component in a lateral direction and has a smoothly concave, semi-spherical proximal surface 92 (FIG. 8) defining a bearing surface which abuts against the hemispherical process 42 defined by the humeral component (FIG. 1). A distal surface 94 of the capitulum portion is smoothly convex and configured to be abutted by and articulate with the head of the radius. In the normal elbow joint, the radius bone would engage the capitulum on the humerus and rotate relative thereto. With the implant in accordance with the present invention, the radius bone abuts the capitulum member on the ulnar component and does not directly articulate with the humeral component or with the humerus bone. Additional bearing surfaces are now defined by the humeral and ulnar components of the implant. The concave surface of the capitulum process also insures lateral stability of the prosthesis after implantation.

The components may be manufactured from a medical grade metal material such as a colbalt chrome alloy. In the alternative, one or both of the components could be fabricated from a medical grade high density polyethylene which possesses self-lubricating properties. Also, it is believed that the articulating surfaces of the components could be fabricated from polyethylene and the remaining portions from metal.

FIG. 1 schematically illustrates the implant in position at the joint between a humerus bone and an ulna bone. As shown therein, the distal end 15 of the humerus is partially resected to receive the humeral component. The bifurcated and smoothly curved nature of the humeral component approximates the configuration of the distal end of the humerus. This reduces the amount of bone material which must be removed. The stem is employed to affix the humeral component to the bone and an acrylic cement may be employed to permanently affix the member. The ulna is also prepared to receive the ulnar component 14. The implant in accordance with the present invention due to its configuration merely requires that the physician remove some of the bone at the semi-lunar notch 104 of the ulna so that it will conform to the posterior surface of the ulnar component. Stem 64 is inserted into the prepared intramedullary canal of the ulna and an acrylic cement may be employed to permanently affix the stem in place. The radius which is positioned laterally of the ulna may, depending on its condition, have a portion of head 89 thereof removed. If the head of the radius is diseased or damaged, a readily available, button implant (not shown) may be used to replace the resected head. Such an implant basically resurfaces the head of the radius. The button implant defines a concave surface which would articulate with the distal surface of capitulum process 90. The head of the radius does not rotate or articulate about the humerus bone or with any portion of the humeral component of the implant.

When the components are interconnected, the sides of hook 70 will be in sliding contact with the sides of the elongated slot defined by the humeral component. The multiple tongue and groove articulation defined by the humeral and ulnar components insures lateral stability of the implant. The hook and aperture prevent dislocation and permit normal flexion and extension of the joint. The ligament system at the elbow must be reconstructed to prevent dislocation and insure joint stability.

The interconnection between the components permits limited proximal distal movement during flexion and extension. This alleviates the problems heretofore experienced with excessive stress being imposed on the bones and on the implant and experienced with permanent hinge-type interconnections. The hook will recenter the implant as the muscles contract and the implant will not dislocate. The capitulum process provides stability for the elbow and prevents proximal migration towards the normal capitulum by the radius. This eliminates the secondary pain which has heretofore been experienced at the wrist. The implants are provided in right and left models since the elbow joints are mirror images of each other.

Although described primarily in the context of replacement of the elbow joint, the hook and aperture interconnection and the tongue and groove tracking features of the present invention could be employed in implants for replacement of other hinge-type joints of the human body. Further, it is believed that various modifications could be made to the components which would not depart from the inventive concepts disclosed herein. For example, the bearing surfaces could be fabricated from a selflubricating high density polyethylene material and the remaining portions of the components could be fabricated from metal. Further, the specific configurations could be varied while still retaining the multiple tongue and groove interfit. Therefore, it is expressely intended that the above description should be considered as that of the preferred embodiment. The true spirit and scope of the present invention may be determined by reference to the appended claims.

The embodiments of the invention in which an exclusive property or privilege is claimed are defined as follows:

1. A total elbow prosthesis for implantation in the humerus and ulna and providing lateral stability during extension and flexion motion of the prosthesis after implantation, said prosthesis comprising:

a humeral component having a main body portion defining a plurality of generally semi-circular distally positioned portions having bearing surfaces;

an ulnar component having a main body portion defining a convex posterior surface adapted to be received within a prepared semi-lunar notch of the ulna and further defining a plurality of semi-circular grooves configured to matingly receive said distally positioned portions of said humeral component; and slipfit hinge means defined by and a part of said ulnar component and said humeral component for detachably and hingedly interconnecting said components together in a slipfit fashion after implantation of the prosthesis thereby alleviating the transmission of excessive stresses to the bones and loosening of the components, said ulnar component further including a capitulum member having a distal surface against which the radius bone articulates after implantation.

2. A total elbow prosthesis as defined by claim 1 wherein said humeral component includes a lateral protruding semi-bulbous portion having a convexly curved surface articulating with a proximal surface of said capitulum member.

3. A total elbow prosthesis as defined by claim 2 wherein said humeral component bearing surfaces and said semi-circular grooves interfit in a tongue and groove fashion.

4. A total elbow prosthesis as defined by claim 2 wherein said slipfit hinge means comprises a hook-shaped member having a proximally extending stem and a curved portion extending anteriorly and distally of said ulnar component main body, said humeral component defining a hook receiving aperture therethrough and an open ended slot, said hook-shaped member extending through said aperture and having a portion received within said slot to hingedly interconnect in a detachable manner said humeral component and said ulnar component.

5. A total elbow prosthesis as defined by claim 4 wherein said humeral component bearing surfaces and said semi-circular grooves interfit in a tongue and groove fashion.

6. A total elbow prosthesis, comprising:

a humeral component having a head and a proximally extending intramedullary canal stem, said head defining an aperture, a depending medial portion and a depending lateral portion on opposite sides of the aperture, said medial and lateral portions having convex bearing surfaces, said head further including a lateral member integral with the lateral portion and defining a smoothly rounded bearing surface; and an ulnar component having a head and a distally extending intramedullary stem, said ulnar component head having a convexly curved posterior surface and a concavely curved anterior surface, a curved hook member extending from said anterior surface, a pair of grooves configured to mate with said medial and lateral portions of said humeral component in a tongue and groove fashion and a capitulum member laterally positioned with respect to said hook member, said capitulum member including a concave bearing surface engaging the bearing surface of said humeral component lateral member and a distal radius articulating surface adapted to abut with the head of the radius bone after implantation.

7. A total elbow prosthesis for replacement of the elbow joint and for preventing proximal migration of the radius bone, said prosthesis comprising:

a humeral component including a main body defining a distal bearing surface;

an ulnar component including a main body defining a bearing surface engaging the bearing surface of said humeral component, said ulnar component further including a lateral process having a distal surface against which the radius bone may abut during flexion and extension motion of the prosthesis; and means on said ulnar and humeral components for interconnecting said components and for permitting rotary, pivotal motion of the components relative to each other in a single plane.

8. A total elbow prosthesis as defined by claim 10 wherein said distal bearing surface is defined by a plurality of semi-circular flange-like portions spaced transversely of said body and wherein the bearing surface of said ulnar component is defined by a plurality of semi-circular grooves dimensioned and positioned to receive said flange-like portions in a tongue and groove fashion.

9. A total elbow prosthesis as defined by claim 8 wherein said humeral component further includes a hemispherical laterally positioned process articulating with a concave surface defined by said ulnar component lateral process.

10. A total elbow prosthesis as defined by claim 9 wherein said ulnar component main body defines a convexly curved posterior surface adapted to fit within a prepared semi-lunar notch of the ulna.

11. A total elbow prosthesis as defined by claim 10 wherein said means for interconnecting comprises said humeral component being generally bifurcated to define an open ended slot and further including a cross member extending across said slot to define a proximal aperture and a semi-circular hook extending from said ulnar component and through said proximal aperture, said hook, said proximal aperture, and said slot dimensioned for relative motion in a single plane.

12. A total elbow prosthesis as defined by claim 8 wherein said means for interconnecting comprises said humeral component being generally bifurcated to define an open ended slot and further including a cross member extending across said slot to define a proximal aperture and a semi-circular hook extending from said ulnar component and through said proximal aperture, said hook, said proximal aperture, and said slot dimensioned for relative motion in a single plane.

13. A total elbow prosthesis as defined by claim 7 wherein said means for interconnecting comprises said humeral component being generally bifurcated to define an open ended slot and further including a cross member extending across said slot to define a proximal aperture and a semi-circular hook extending from said ulnar component and through said proximal aperture, said hook, said proximal aperture, and said slot dimensioned for relative motion in a single plane.

14. An articulating prosthesis for replacement of a hinge joint having movement in a plane as adjacent bone ends articulate with respect to each other, said prosthesis comprising:

a first component having a body and a stem adapted for implantation in one of the bones at the joint, said first component defining an elongated open ended slot opening through the body at an end opposite the stem and further including a cross piece extending transversely of the slot to define an aperture, said slot having opposed sides, said body defining at least two semi-circular flanges each having curved bearing surfaces; and a second component having a body and a stem adapted for implantation in the other of the bones at the joint, said body defining a concavely curved surface having at least two inwardly directed semi-circular grooves dimensioned to receive the flanges of said first component and an outwardly directed hook member integral with the body of said second component, said hook dimensioned to fit within said slot, around said cross piece and through said aperture, said hook preventing dislocation of said components from each other after implantation, permitting said components to be detachably interconnected, and alleviating transmission of excessive stress to the bone, said first component further including a laterally positioned process defined by said body of said first component, said process having a spherical-like surface, said second component including a laterally positioned and extending process having a generally concavely curved surface engaged by the laterally positioned process of said first component.

15. An articulating prosthesis as defined by claim 14 wherein said prosthesis is adapted for replacement of the elbow joint and said process of said second component includes a convexly curved lower surface adapted to be engaged by the radius bone.

* * * * *

UNITED STATES PATENT AND TRADEMARK OFFICE

CERTIFICATE OF CORRECTION

PATENT NO. : 4,280,231

DATED : July 28, 1981

INVENTOR(S) : Alfred B. Swanson

It is certified that error appears in the above—identified patent and that said Letters Patent is hereby corrected as shown below:

Column 1, line 14:

"tissues" should be --tissue--;

Column 7, line 57:

"10" should be --7--;

Column 8, line 58:

After "spherical-like" insert --bearing--.

Signed and Sealed this

*Sixth* Day of *October 1981*

[SEAL]

*Attest:*

GERALD J. MOSSINGHOFF

*Attesting Officer* *Commissioner of Patents and Trademarks*